United States Patent
Coffey et al.

(10) Patent No.: US 7,799,329 B2
(45) Date of Patent: Sep. 21, 2010

(54) VIRUSES FOR THE TREATMENT OF CELLULAR PROLIFERATIVE DISORDERS

(75) Inventors: Matthew C. Coffey, Calgary (CA); Bradley G. Thompson, Calgary (CA)

(73) Assignee: Oncolytics Biotech Inc., Calgary, Alberta (CA)

(*) Notice: Subject to any disclaimer, the term of this patent is extended or adjusted under 35 U.S.C. 154(b) by 0 days.

(21) Appl. No.: 11/807,770

(22) Filed: May 30, 2007

(65) Prior Publication Data

US 2008/0019980 A1  Jan. 24, 2008

Related U.S. Application Data

(60) Division of application No. 11/557,467, filed on Nov. 7, 2006, which is a division of application No. 10/418,290, filed on Apr. 18, 2003, now Pat. No. 7,252,817, which is a continuation of application No. 09/708,663, filed on Nov. 9, 2000, now Pat. No. 6,596,268.

(60) Provisional application No. 60/164,878, filed on Nov. 12, 1999.

(51) Int. Cl.
*A61K 48/00* (2006.01)
*A61K 39/235* (2006.01)
*A61K 39/12* (2006.01)
*A61K 39/00* (2006.01)

(52) U.S. Cl. ............... 424/232.1; 424/233.1; 424/93.1; 424/131.1

(58) Field of Classification Search ................. 435/975, 435/320.1; 424/93.1
See application file for complete search history.

(56) References Cited

U.S. PATENT DOCUMENTS

| | | | |
|---|---|---|---|
| 5,023,252 A | 6/1991 | Hseih | |
| 5,585,096 A | 12/1996 | Martuza et al. | |
| 5,856,181 A | 1/1999 | McCormick | |
| 6,136,307 A | 10/2000 | Lee et al. | |
| 6,245,543 B1 | 6/2001 | Drake et al. | |
| 6,428,968 B1 | 8/2002 | Molnar-Kimber et al. | |
| 6,455,038 B1 | 9/2002 | Lee et al. | |
| 6,723,316 B2 | 4/2004 | Laquerre et al. | |
| 6,774,119 B1 | 8/2004 | Wechsler et al. | |
| 6,838,279 B2 | 1/2005 | Wechsler et al. | |

FOREIGN PATENT DOCUMENTS

| | | |
|---|---|---|
| EP | 0 514 603 | 11/1992 |
| EP | 0 828 005 | 3/1998 |
| WO | WO 96/00007 | 1/1996 |
| WO | WO 97/12623 | 4/1997 |
| WO | WO 98/37031 | 10/1997 |
| WO | WO 97/45142 | 12/1997 |
| WO | WO 98/50053 | 11/1998 |
| WO | WO 99/08692 | 2/1999 |
| WO | WO 99/18799 | 4/1999 |
| WO | WO99/18799 * | 4/1999 |
| WO | WO 99/45783 | 9/1999 |
| WO | WO 99/55910 | 11/1999 |
| WO | WO 99/67372 | 12/1999 |
| WO | WO 01/35970 | 5/2001 |

OTHER PUBLICATIONS

Bouvet et al. Gene Ther. Feb. 1998, vol. 5, pp. 189-195.*
Jooss et al. Human Gene Ther. Aug. 20, 1996;7(13):1555-1566.*
Eloit et al. (J. Virol. Jul. 1997;71(7):5375-5381.*
Wildner et al. Cancer Research 59, 410-413, Jan. 1, 1999.*
Gurnani et al. Cancer Chemother. Pharmacol. 1999, vol. 44 (2), pp. 143-151.*
Ghadge et al. J. Virol. 1994, vol. 68, No. 7, pp. 4137-4151.*
Ikeda et al. Nature medicine 1999, vol. 5, No. 8, pp. 881-887.*
Valenzuela et al. Nucleic Acids Research 1986, vol. 4, No. 2, pp. 843-852.*
Luo et al. J. Neurochem, 1998, vol. 71, pp. 980-990.*
Wislez et al. The Intersection of EGFR and the ras Signaling Pathway in EGFR Signaling Networks in chaper 7 of Cancer Therapy edited by John D. Haley et al. 2008, pp. 89-95.*
Cascallo et al., "Deletion of VAI and VAII RNA Genes in the Design of Oncolytic Adenoviruses," *Human Gene Therapy*, 17:929-940 (2006).
Henriksson et al., "Ras Effector Pathway Activation by Epidermal Growth Factor is Inhibited in Vivo by Exoenzyme S ADP-Ribosylation of Ras," *Biochem Journal*, 347:217-222 (2000).

(Continued)

*Primary Examiner*—Robert B Mondesi
*Assistant Examiner*—Bao Li
(74) *Attorney, Agent, or Firm*—McKeon Meunier Carlin & Curfman LLC

(57) ABSTRACT

Methods for treating cell proliferative disorders by administering virus to proliferating cells having an activated Ras-pathway are disclosed. The virus is administered so that it ultimately directly contacts proliferating cells having an activated Ras-pathway. Proliferative disorders include but are not limited to neoplasms. The virus is selected from modified adenovirus, modified HSV, modified vaccinia virus and modified parapoxvirus orf virus. Also disclosed are methods for treating cell proliferative disorders by further administering an immunosuppressive agent.

9 Claims, 1 Drawing Sheet

OTHER PUBLICATIONS

Kibler et al., "Double-Stranded RNA Is a Trigger for Apoptosis in Vaccinia Virus-Infected Cells," *Journal of Virology*, 71(3): 1992-2003 (1997).

Krypuy et al., "High Resolution Melting Analysis for the Rapid and Sensitive Detection of Mutations in Clinical Samples: KRAS Codon 12 and 13 Mutations in Non-Small Cell Lung Cancer," *BMC Cancer*, 6:295 (2006).

Thimmappaya et al., "Adenovirus VAI RNA is Required for Efficient Translation of Viral mRNAs at Late Times after Infection," *Cell*, 31:543-551 (1982).

Timiryasova et al., "Antitumor Effect of Vaccinia Virus in Glioma Model," *Oncology Research*, 11:133-144 (1999).

Andreansky, S.S., et al. (1996). The application of genetically engineered herpes simplex viruses to the treatment of experimental brain tumors. Proc Natl Acad Sci USA 93(21):11313-11319.

Alemany, R. et al. (1999). Complementary adenoviral vectors for oncolysis. Cancer Gene Ther. 6(1):21-25.

Barbacid, M. (1987). Ras genes. Annu Rev Biochem. 56:779-827.

Battcock et al., 2006, J. Virol. 80(9):4422-4430.

Beattie, E., et al. (1991). Vaccinia virus-encoded eIF-2α homolog abrogates the antiviral effect of interferon. Virology. 183(1):419-422.

Black, T.L., et al. (1993). Degradation of the interferon-induced 68,000-M(r) protein kinase by poliovirus requires RNA. J Virol. 67(2):791-800.

Bos, J.L. (1989). Ras oncogenes in human cancer: a review. Cancer Res. 49(17):4682-4689.

Boviatsis, E.J., et al. (1994). Antitumor activity and reporter gene transfer into rat brain neoplasms inoculated with herpes simplex virus vectors defective in thymidine kinase or ribonucleotide reductase. Gene Ther. 5:323-321.

Carroll, N. M., et al. (1997). The effect of ganciclovir on herpes simplex virus-mediated oncolysis. J Surg Res. 69(2):413-417.

Cascallo et al., 2003, Cancer Res. 63:5544-5550.

Cassady, K.A., et al. (1998). The second-site mutation in the herpes simplex virus recombinants lacking the $_{\gamma 1}34.5$ genes precludes shutoff of protein synthesis by blocking the phosphorylation of eIF-2α. J Virol. 72(9):7005-7011.

Chahlavi, A., et al. (1999). Replication-competent herpes simplex virus vector G207 and cisplatin combination therapy for head and neck squamous cell carcinoma. Neoplasia. 1(2):162-169.

Chang, H.W. and Jacobs, B.L. (1993). Identification of a conserved motif that is necessary for binding of the vaccinia virus E3L gene products to double-stranded RNA. Virology. 194(2):537-547.

Chaubert, P. et al. (1994). K-ras mutations and p53 alterations in neoplastic and nonneoplastic lesions associated with longstanding ulcerative colitis. Am J Pathol. 144(4):767-775.

Chong, K.L., et al. (1992). Human p68 kinase exhibits growth suppression in yeast and homology to the translational regulator GCN2. EMBO J. 11(4):1553-1562.

Chung, R.Y., et al. (1999). B-*myb* promoter retargeting of herpes simplex virus $_{\gamma}34.5$ gene-mediated virulence toward tumor and cycling cells. J Virol. 73(9):7556-7564.

Davies, M.V., et al. (1991). The effect of poliovirus proteinase 2Apro expression on cellular metabolism. Inhibition of DNA replication, RNA polymerase II transcription, and translation. J Biol Chem. 266(22):14714-14720.

Davies, M.V., et al. (1993). The E3L and K3L vaccinia virus gene products stimulate translation through inhibition of the double-stranded RNA-dependent protein kinase by different mechanisms. J Virol. 67(3):1688-1692.

Farassati et al., Nat. Cell Biol. 3:745-750, (2001).

Gura, T. (1997). Systems for identifying new drugs are often faulty. Science. 278(5340):1041-1042.

Haig, D.M., et al. (1998). The orf virus OV20.0L gene product is involved in interferon resistance and inhibits an interferon-inducible, double-stranded RNA-dependent kinase. Immunology. 93(3):335-340.

Hall-Jackson, C.A., et al. (1998). Induction of cell death by stimulation of protein kinase C in human epithelial cells expressing a mutant ras oncogene: a potential 'therapeutic target. Br J Cancer. 78(5):641-651.

He, B., et al. (1997). The $_{\gamma 1}34.5$ protein of herpes simplex virus 1 complexes with protein phosphatase 1α to dephosphorylate the α subunit of the eukaryotic translation initiation factor 2 and preclude the shutoff of protein synthesis by double-stranded RNA-activated protein kinase. Proc Natl Acad Sci USA. 94(3):843-848.

Ikeda, K., et al. (1999). Oncolytic virus therapy of multiple tumors in the brain requires suppression of innate and elicited antiviral responses. Nat Med. 5(8):881-887.

Jagus, R., and Gray, M.M. (1994). Proteins that interact with PKR. Biochimie. 76(8):779-791.

Janes, P.W., et al. (1994). Activation of the Ras signalling pathway in human breast cancer cells overexpressing erbB-2. Oncogene. 9(12):3601-3608.

Katze, M.G., et al. (1987). Adenovirus VAI RNA complexes with the 68 000 Mr protein kinase to regulate its autophosphorylation and activity. EMBO J. 6(3):689-697.

Katze, M.G. (1995). Regulation of the interferon-induced PKR: can viruses cope? Trends Microbiol. 3(2):75-78.

Kawagishi-Kobayashi, M., et al. (1997). Regulation of the protein kinase PKR by the vaccinia virus pseudosubstrate inhibitor K3L is dependent on residues conserved between the K3L protein and the PKR substrate eIF2α. Mol Cell Biol. 17(7):4146-4158.

Khoobyarian, N., et al. (1975). Inhibition of melanoma growth in hamsters by type-2 adenovirus. J Surg Oncol. 7(5):421-425.

Kirn, D.H., and McCormick., F. (1996). Replicating viruses as selective cancer therapeutics. Mol Med Today 2(12):519-527.

Lee, J.M., and Bernstein, A. (1993). p53 mutations increase resistance to ionizing radiation. Proc Natl Acad Sci USA. 90(12):5742-5746.

Lee, T.G., et al. (1994). The 58,000-dalton cellular inhibitor of the interferon-induced double-stranded RNA-activated protein kinase (PKR) is a member of the tetratricopeptide repeat family of proteins. Mol Cell Biol. 14(4):2331-2342.

Levitzki, A. (1994). Signal-transduction therapy. A novel approach to disease management. Eur J Biochem. 226(1):1-13.

Lowe, S.W., et al. (1994). p53 status and the efficacy of cancer therapy in vivo. Science. 266(5186):807-810.

Martuza, R.L., et al. (1991). Experimental therapy of human glioma by means of a genetically engineered virus mutant. Science 252(5007):854-856.

Mathews, M.B., and Shenk, T. (1991). Adenovirus virus-associated RNA and translation control. J Virol. 65(11):5657-5662.

Mills, N. E., et al. (1995). Increased prevalence of K-ras oncogene mutations in lung adenocarcinoma. Cancer Res. 55(7):1444-14447.

Mundschau, L.J., and Faller, D.V. (1992). Oncogenic ras induces an inhibitor of double-stranded RNA-dependent eukaryotic initiation factor 2α-kinase activation. J Biol Chem. 267(32):23092-23098.

Mundschau, L.J., and Faller, D.V. (1994). Endogenous inhibitors of the dsRNA-dependent eIF-2α protein kinase PKR in normal and ras-transformed cells. Biochimie. 76(8):792-800.

Nanduri, S., et al. (1998). Structure of the double-stranded RNA-binding domain of the protein kinase PKR reveals the molecular basis of its dsRNA-mediated activation. EMBO J. 17(18):5458-5465.

Proud, C.G. (1995). PKR: a new name and new roles. Trends Biochem Sci. 20(6):241-246.

Rahman, A., et al. (1995). Effect of single-base substitutions in the central domain of virus-associated RNA I on its function. J Virol. 69(7):4299-4307.

Raybaud-Diogène, H., et al. (1997). Markers of radioresistance in squamous cell carcinomas of the head and neck: a clinicopathologic and immunohistochemical study. J Clin Oncol. 15(3):1030-1038.

Redpath, N. T., and Proud, C.G. (1994). Molecular mechanisms in the control of translation by hormones and growth factors. Biochim Biophys Acta. 1220(2):147-162.

Strong, J.E., et al. (1998). The molecular basis of viral oncolysis: usurpation of the Ras signaling pathway by reovirus. EMBO J. 17(12):3351-3362.

Tanaka, N., et al. (1994). Immunotherapy of a vaccinia colon oncolysate prepared with interleukin-2 gene-encoded vaccinia virus and interferon-α increases the survival of mice bearing syngeneic colon adenocarcinoma (abstract). Immunother Emphasis Tumor Immunol. 16(4):283-293.

Toda, M., et al. (1998). Treatment of human breast cancer in a brain metastatic model by G207, a replication-competent multimutated herpes simplex virus 1. Hum Gene Ther. 9(15):2177-2185.

Toyoizumi, Takane et al., "Combined Therapy with Chemotherapeutic Agents and Herpes Simplex Virus Type 1 ICP34.5 Mutant (HSV-1716) in Human Non-Small Cell Lung Cancer", *Human Gene Therapy*, vol. 10:pp. 3013-3029 (1999).

Wiesmuller, L., and Wittinghofer, F. (1994). Signal transduction pathways involving Ras. mini review. Cell Signal. 6(3):247-267.

Williams, B.R.G. (1997). Role of the double-stranded RNA-activated protein kinase (PKR) in cell regulation. Biochem Soc Trans. 25(2):509-513.

Wu, S., et al. (1998). Identification and requirement of three ribosome binding domains in dsRNA-dependent protein kinase (PKR). Biochemistry. 37(39):13816-13826.

Zhang, J.F., et al. (1996). Treatment of a human breast cancer xenograft with an adenovirus vector containing an interferon gene results in rapid regression due to viral oncolysis and gene therapy. Proc Natl Acad Sci US A. 93(9):4513-4518.

Diven et al., "An overview of poxviruses" *J. Am. Acad. Dermatol.* 44(1):1-16 (2001).

Slattery et al., "Milkers' nodules complicated by erythema multiforme and graft-versus-host disease after allogenic hematopoietic stem cell transplantation for multiple myeloma" *CID* 40:63-66 (2005).

Lederman, et al., "Progressive orf virus infection in a patient with lymphoma: successful treatment using imiquimod" *CID* 44:e100-e103 (2007).

Luo et al., "D2 dopamine receptors stimulate mitogenesis through pertussis toxin-sensitive g proteins and ras-involved erk and sap/jnk pathways in rat c6-d21 glioma cells" *J. Neurochem.* 71:980-990 (1998).

Valenzuela et al., "Four human carcinoma cell lines with novel mutations in position 12 of c-K-ras oncogene" *Nucleic Acids Research* 4(2):843-852 (1986).

Wislez et al., "The intersection of EGFR and the ras signaling pathway in EGFR signaling networks" Chapter 7, Cancer Therapy, Ed. John Haley et al., pp. 89-95 (2008).

\* cited by examiner

VIRUSES FOR THE TREATMENT OF CELLULAR PROLIFERATIVE DISORDERS

CROSS REFERENCE TO RELATED APPLICATIONS

This application is a divisional of application Ser. No. 10/418,290, filed on Apr. 18, 2003, which is a continuation of application Ser. No. 09/708,663, filed on Nov. 9, 2000, now U.S. Pat. No. 6,596,268 which claims the benefit of U.S. Provisional Application No. 60/164,878, filed Nov. 12, 1999. The disclosure of each of the above applications is incorporated herein by reference in their entirety.

BACKGROUND OF THE INVENTION

Field of the Invention

The present invention pertains to methods for treating cellular proliferative disorders in a mammal that are mediated by Ras-activation using mutant viruses.

REFERENCES

The following publications, patent applications and patents are cited in this application:
1. Beattie, E. et al., *Virology* (1991) 183:419-422
2. Black, T. L., et al., *J. Virol*. (1993) 67:791-800
3. Chang, H. W. and Jacobs, B. L. *Virology* (1993) 194:537-547
4. Chong, K. L. et al., *EMBO J.* (1992) 11:1553-1562
5. Davies, M. V. et al., *JBC* (1991) 266:14714-14720
6. Davies, M. V. et al., *J. Virology* (1993) 67:1688-1692
7. Jagus, R. and Gray M. M. *Biochimie* (1994) 76:779-791
8. Katze, M. G. et al., *EMBO J* (1987) 6:689-697
9. Katze M. G. et al., *Trends in Microbiology* (1995) 3:75-78
10. Lee, T. G. et al., *MCB* (1994) 14:2331-2342
11. Mundshau, L. J. and Faller, D. V., *JBC* (1992) 267:23092-23098
12. Mundshau, L. J. and Faller, D. V., *Biochimie* (1994) 76:792-800
13. Nanduri, S. *EMBO J.* (1998) 17:5458-5465
14. Proud, D. G. *Trends in Biochemical Sciences*, (1995) 20:241-246
15. Redpath, N. T. and Proud, D. G. *Biochimica et Biophysica Acta*, (1994) 1220:147-162
16. Strong, J. E. et al., *EMBO* (1998) 17:3351-3362
17. Williams, B. R., *Biochemical Society Transactions* (1997) 25:509-513
18. Wiessmuller, L. and Wittinghofer, F., *Cellular Signaling* (1994) 6(3):247-267
19. Barbacid, M., *A Rev. Biochem*. (1987) 56:779-827
20. Millis, N. E. et al., *Cancer Res*. (1995) 55:1444
21. Chaubert, P. et al., *Am. J. Path*. (1994) 144:767
22. Bos, J., *Cancer Res*. (1989) 49:4682
23. Levitzki A., *Eur. J. Biochem*. (1994) 226:1
24. James P. W., et al., (1994) *Oncogene* 9:3601
25. Lee J. M. et al., *PNAS* (1993) 90:5742-5746
26. Lowe S. W. et al., *Science*, (1994) 266:807-810
27. Raybaud-Diogene H. et al. *J. Clin. Oncology*, (1997) 15(3):1030-1038
28. Brooks et al., eds. "Jawetz, Melnick, & Adelberg's Medical Microbiology," (1998)
29. He, B. et al, *PNAS* (1997) 94:843-848
30. Haig, D. M. et al., *Immunology* (1998) 93:335-340
31. Kawagishi-Kobayashi, M. et al., *MCB* (1997) 17:4146-4158
32. Martuza et al., European Patent Application Publication Number EP 0 514 603, published Nov. 25, 1992

All of the above publications, patent applications and patents are herein incorporated by reference in their entirety to the same extent as if each individual publication, patent application or patent was specifically and individually indicated to be incorporated by reference in its entirety.

STATE OF THE ART

Normal cell proliferation is regulated by a balance between growth promoting proto-oncogenes and growth-constraining tumor-suppressor genes. Tumorigenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Genetic alteration of the proto-oncogene Ras is believed to contribute to approximately 30% of all human tumors.[18, 19] The role that Ras plays in the pathogenesis of human tumors is specific to the type of tumor. Activating mutations in Ras itself are found in most types of human malignancies, and are highly represented in pancreatic cancer (80%), sporadic colorectal carcinomas (40-50%), human lung adenocarcinomas (15-24%), thyroid tumors (50%) and myeloid leukemia (30%).[20, 21, 22] Ras activation is also demonstrated by upstream mitogenic signaling elements, notably by tyrosine receptor kinases (RTKs). These upstream elements, if amplified or overexpressed, ultimately result in elevated Ras activity by the signal transduction activity of Ras. Examples of this include overexpression of PDGFR in certain forms of glioblastomas, as well as in c-erbB-2/neu in breast cancer.[22, 23, 24]

Protein kinase R ("PKR") is a serine/threonine kinase that is induced in the presence of interferon.[7, 9, 17] The primary cellular substrate of this kinase is the α subunit of the translation initiation factor eIF-2 on Serine 5.[14, 15, 17] Phosphorylation of eIF-2 results in a rapid inhibition of protein synthesis by preventing its participation in further rounds of translation initiation.

Although PKR is normally inactive, it becomes rapidly activated in the presence of double stranded RNA (dsRNA) or RNAs that exhibit extensive secondary structures, elements that are frequently produced as the result of viral infection. The amino-terminal of PKR contains a double stranded RNA binding domain (dsRBD) that allows this interaction with dsRNA. Binding of PKR to dsRNA element allows PKR to undergo a conformational change that facilitates autophosphorylation and subsequent phosphorylation of eIF-2.[4] Further, it appears that the cooperative binding of two PKR molecules to one dsRNA molecule is required to achieve activation since the addition of dsRNA to PKR results in the dsRNA/PKR activation complex to be found in a 2:1 ratio of protein to dsRNA.[17]

Double-stranded RNA (dsRNA) viruses are not entirely susceptible to the host cell PKR because they have evolved a number of different strategies to inhibit PKR activation in response to their presence:

(1) In the case of adenovirus, a viral product, VAI RNA, is synthesized in large amounts. These VAI RNA elements, with their extensive secondary structure and short length inactivate PKR by acting as a competitive inhibitor of the full length viral dsRNA.[8] The short length of the VAI RNA elements is critical, as there is a minimum length dsRNA which activates PKR. PKR bound to VAI RNA is not activated;

(2) Vaccinia virus encodes two gene products, K3L and E3L to down-regulate PKR with different mechanisms. The K3L gene product has limited homology with the N-terminal region of eIF-2α and may act as a pseudosubstrate for PKR.[1, 5] The E3L gene product is a dsRNA-binding protein and apparently functions by sequestering activator dsRNAs;[3, 6]

(3). Herpes simplex virus (HSV) gene $_{\gamma 1}$34.5 encodes the gene product infected-cell protein 34.5 (ICP34.5) that can prevent the antiviral effects exerted by PKR; and (4) The parapoxvirus orf virus encodes the gene OV20.0L that is involved in blocking PKR activity.[30]

It has been demonstrated that in Ras transformed cells, dsRNA-mediated activation of PKR was blocked at the level of autophosphohrylation.[16]

PKR is one of many cellular proteins that is induced in the presence of interferon ("IFN"). In normal cells, PKR is normally induced and activated in the presence of IFN. In Ras-mediated tumor cells, however, PKR is induced in the presence of IFN but the activation of PKR is reversed or inhibited. Accordingly, Ras-mediated tumors are unable to activate a PKR response.

It has been observed that pre-treating cells with IFN to induce the transcription and translation of PKR prevents reovirus infection. PKR was activated in cells that were pre-treated with IFN, suggesting that there may be a "quantity effect." When the cells were not pre-treated with IFN, reovirus was able to replicate quickly enough such that there was not enough time to allow sufficient PKR to be synthesized. Additionally, the PKR already present in the cell was not activated. This observation suggests that the cells are not deficient in the IFN response per se, since PKR is only one element of the IFN response and PKR apparently acted normally if the cells were pre-treated.

Current methods of treatment for neoplasia include surgery, chemotherapy and radiation. Surgery is typically used as the primary treatment for early stages of cancer; however, many tumors cannot be completely removed by surgical means. In addition, metastatic growth of neoplasms may prevent complete cure of cancer by surgery. Chemotherapy involves administration of compounds having antitumor activity, such as alkylating agents, antimetabolites, and anti-tumor antibiotics. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy cannot be used to treat many neoplasms, however, because of the sensitivity of tissue surrounding the tumor. In addition, certain tumors have demonstrated resistance to radiotherapy and such may be dependent on oncogene or anti-oncogene status of the cell.[25, 26, 27] Martuza et al., EP 0 514 603[32], generically describes methods for selectively killing neoplastic cells which utilize altered viruses that are capable of replication in neoplastic cells while sparing surrounding normal tissue.

Accordingly, it has been found that viruses which have evolved certain mechanisms of preventing PKR activation are likely rendered replication incompetent when these same mechanisms are prevented or mutated. Mutation or deletion of the genes responsible for antagonizing PKR should prevent viral replication in cells in which the PKR activity is normal (i.e. normal cells). However, if infected cells are unable to activate the antiviral response mediated through PKR (i.e., Ras-mediated tumor cells), then these mutant viruses should replicate unheeded and cause cell death. Therefore, these mutant viruses can replicate preferentially in Ras-transformed cells where it is determined that PKR is unable to function.

In view of the drawbacks associated with the current means for treating neoplastic growth, the need still exists for improved methods for the treatment of most types of cancers.

SUMMARY OF THE INVENTION

This invention is directed to a method for treating a Ras-mediated cell proliferative disorder in a mammal, comprising administering to proliferating cells in a mammal having a Ras-activated pathway an effective amount of one or more viruses selected from the group consisting of modified adenovirus, modified HSV, modified vaccinia virus and modified parapoxvirus orf virus under conditions which result in substantial lysis of the proliferating cells.

The virus is attenuated or modified such that modified adenovirus comprises a mutant gene encoding VAI RNA, the modified HSV comprises a mutation in the gene $_{\gamma 1}$34.5, the modified vaccinia virus comprises a mutant gene selected from the group consisting of E3L and K3L, and the modified parapoxvirus orf virus comprises a mutation in the OV20.OL gene.

The virus may be modified such that the virion is packaged in a liposome or micelle, or the proteins of the outer capsid have been mutated. The virus can be administered in a single dose or in multiple doses. The cell proliferative disorder may be a neoplasm. Both solid and hematopoietic neoplasms can be targeted.

Also provided is a method of treating a neoplasm having an activated Ras-pathway in a human, comprising administering to the neoplasm an effective amount of virus selected from the group consisting of modified adenovirus, modified HSV, modified vaccinia virus and modified parapoxvirus orf virus, to result in substantial oncolysis of the neoplastic cells.

The virus may be administered by injection into or near a solid neoplasm.

Also provided is a method of inhibiting metastasis of a neoplasm having an activated Ras-pathway in a mammal, comprising administering to the neoplastic cells in a mammal a virus selected from the group consisting of modified adenovirus, modified HSV, modified vaccinia virus and modified parapoxvirus orf virus, in an amount sufficient to result in substantial lysis of the neoplasm.

Also provided is a method of treating a neoplasm suspected of having an activated Ras-pathway in a mammal, comprising surgical removal of the substantially all of the neoplasm and administration of a virus selected from the group consisting of modified adenovirus, modified HSV, modified vaccinia virus and modified parapoxvirus orf virus, to the surgical site in an amount sufficient to result in substantial oncolysis of any remaining neoplasm.

Also provided is a pharmaceutical composition comprising a virus selected from the group consisting of modified adenovirus, modified HSV, modified vaccinia virus and modified parapoxvirus orf virus, a chemotherapeutic agent and a pharmaceutically acceptable excipient.

Also provided is a pharmaceutical composition comprising a virus selected from the group consisting of modified adenovirus, modified HSV, modified vaccinia virus and modified parapoxvirus orf virus, and a pharmaceutically acceptable excipient.

Further, this invention includes a kit comprising a pharmaceutical composition comprising a virus selected from the group consisting of modified adenovirus, modified HSV, modified vaccinia virus and modified parapoxvirus orf virus, and a chemotherapeutic agent.

Additionally, this invention provides a kit comprising a pharmaceutical composition comprising a virus selected from the group consisting of modified adenovirus, modified HSV, modified vaccinia virus and modified parapoxvirus orf virus and an anti-antivirus antibody.

Also provided is a method for treating a population of cells comprising a neoplasm suspected of having an activated Ras-pathway in vitro comprising administering to said population of cells in vitro a virus selected from the group consisting of modified adenovirus, modified HSV, modified vaccinia virus and modified parapoxvirus orf virus in an amount sufficient to result in substantial lysis of the neoplasm.

The invention is also directed to methods of treating a Ras-mediated proliferative disorder in a mammal, by immunosuppressing, immunoinhibiting or otherwise rendering the mammal immunodeficient and, concurrently or subsequently, administering a virus selected from the group consisting of modified adenovirus, modified HSV, modified vaccinia virus and modified parapoxvirus orf virus in an amount sufficient to result in substantial lysis of the neoplasm. In particular, it is directed to method for treating a Ras-mediated proliferative disorder in a mammal, by
   a) performing a step selected from the group consisting of:
      i) administering to the proliferating cells in said mammal an effective amount of an immune suppressive agent;
      ii) removing B-cells or T-cells from said mammal;
      iii) removing anti-virus antibodies from said mammal;
      iv) removing antibodies from said mammal;
      v) administering anti-antivirus antibodies to said mammal; and
      vi) suppressing the immune system of the mammal; and
   b) administering to the proliferating cells in said mammal an effective amount of one or more viruses selected from the group consisting of modified adenovirus, modified HSV, modified vaccinia virus and modified parapoxvirus orf virus under conditions which result in substantial lysis of the proliferating cells.

The methods and pharmaceutical compositions of the invention provide an effective means to treat neoplasia having an activated Ras-pathway, without the side effects associated with other forms of cancer therapy.

The foregoing and other objects, features and advantages of the invention will be apparent from the following more particular description of preferred embodiments of the invention, as illustrated in the accompanying figure.

DETAILED DESCRIPTION OF THE INVENTION

Figure 1:
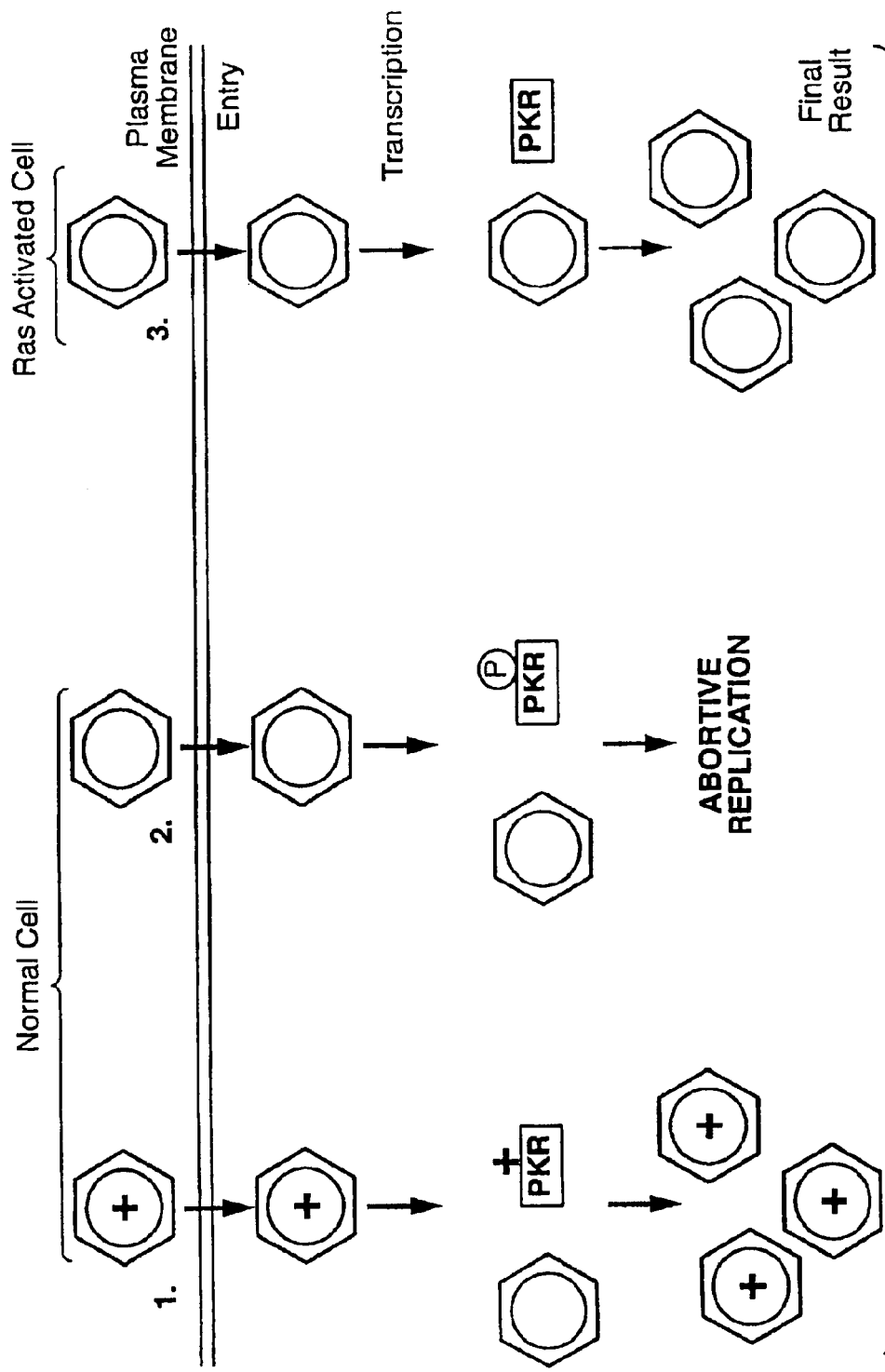
FIG. 1 is a depiction of the molecular basis of VAI defective adenovirus oncolysis.

The invention pertains to methods of treating a Ras-mediated proliferative disorder in a mammal, by administering a virus selected from the group consisting of modified adenovirus, modified HSV, modified vaccinia virus and modified parapoxvirus orf virus, to the proliferating cells.

DEFINITIONS

The following terms used herein are defied as follows:
"Adenovirus" is a double stranded DNA virus of about 3.6 kilobases. In humans, adenoviruses can replicate and cause disease in the eye and in the respiratory, gastrointestinal and urinary tracts. About one-third of the 47 known human serotypes are responsible for most cases of human adenovirus disease.[28] The adenovirus encodes several gene products that counter antiviral host defense mechanisms. The virus-associated RNA (VAI RNA or VA $RNA_1$) of the adenovirus are small, structured RNAs that accumulate in high concentrations in the cytoplasm at late time after adenovirus infection. These VAI RNA bind to the to the double stranded RNA (dsRNA) binding motifs of PKR and block the dsRNA-dependent activation of PKR by autophosphorylation. Thus, PKR is not able to function and the virus can replicate within the cell. The overproduction of virons eventually leads to cell death. The attenuated or modified adenovirus is unable to replicate in cells which do not have an activated Ras-pathway. However, attenuated or modified adenovirus can replicate in cells with an activated Ras-pathway.

The term "attenuated adenovirus" or "modified adenovirus" means that the gene product or products which prevent the activation of PKR are lacking, inhibited or mutated such that PKR activation is not blocked. Preferably, the VAI RNA's are not transcribed. Such attenuated or modified adenovirus would not be able to replicate in normal cells that do not have an activated Ras-pathway, however, it would be able to infect and replicate in cells having an activated Ras-pathway.

"Herpes simplex virus" (HSV) refers to herpes simplex virus-1 (HSV-1) or herpes simplex virus-2 (HSV-2). HSV gene $_{\gamma 1}34.5$ encodes the gene product infected-cell protein 34.5 (ICP34.5) that can prevent the antiviral effects exerted by PKR.

ICP34.5 has a unique mechanism of preventing PKR activity by interacting with protein phosphatase 1 and redirecting it activity to dephosphorylate eIF-2α.[29] In cells infected with either wild-type or the genetically engineered virus from which the $_{\gamma 1}34.5$ genes were deleted, eIF-2α is phosphorylated and protein synthesis is turned off in cells infected with $_{\gamma 1}34.5$ minus virus. It would be expected that the $_{\gamma 1}34.5$ minus virus would be replication competent in cells with an activated Ras pathway in which the activity of ICP34.5 would be redundant. HSV is unable to replicate in cells which do not have an activated Ras-pathway. Thus, HSV can replicate in cells which have an activated Ras-pathway.

The term "attenuated HSV" or "modified HSV" means that the gene product or products which prevent the activation of PKR are lacking, inhibited or mutated such that PKR activation is not blocked. Preferably, the HSV gene $_{\gamma 1}34.5$ is not transcribed. Such attenuated or modified HSV would not be able to replicate in normal cells that do not have an activated Ras-pathway, however, it would be able to infect and replicate in cells having an activated Ras-pathway.

"Parapoxvirus Orf Virus" is a poxvirus. It is a virus that induces acute cutaneous lesions in different mammalian species, including humans. Parpoxvirus orf virus naturally infects sheep, goats and humans through broken or damaged skin, replicates in regenerating epidermal cells and induces pustular leasions that turns to scabs.[30] The parapoxvirus orf virus encodes the gene OV20.0L that is involved in blocking PKR activity.[30] The parapoxvirus orf virus is unable to replicate in cells which do not have an activated Ras-pathway. Thus, the parapoxvirus orf virus replicate in cells which have an activated Ras-pathway.

The term "attenuated parapoxvirus orf virus" or "modified parapoxvirus orf virus" means that the gene product or products which prevent the activation of PKR are lacking, inhibited or mutated such that PKR activation is not blocked. Preferably, the gene OV20.0L is not transcribed. Such attenuated or modified parapoxvirus orf virus would not be able to replicate in normal cells that do not have an activated Ras-pathway, however, it would be able to infect and replicate in cells having an activated Ras-pathway.

"Vaccinia virus" refers to the virus of the orthopoxvirus genus that infects humans and produces localized lesions.[28] Vaccinia virus encodes two genes that play a role in the down regulation of PKR activity through two entirely different mechanisms. E3L gene encodes two proteins of 20 and 25 kDa that are expressed early in infection and have dsRNA binding activity that can inhibit PKR activity. Deletion or disruption of the E3L gene creates permissive viral replication in cells having an activated Ras pathway. The K3L gene of vaccinia virus encodes pK3, a pseudosubstrate of PKR.

Deletion of residues which disrupt E3 function to inhibit the dsRNA binding. Additionally, since the amino terminal region of E3 protein interacts with the carboxy-terminal region domain of PKR, deletion or point mutation of this domain prevents anti-PKR function. Chang et al., *PNAS* 89:4825-4829 (1992); Chang et al., *Virol.* 194:537-547 (1993); Chang et al. *J. Virol.* 69:6605-6608 (1995); Sharp et al. *Virol.* 250:302-315 (1998); and Romano et al., *Molecular and Cellular Bio.*, 18(12):7304-7316 (1998). The K3L gene of vaccinia virus encodes pK3, a pseudosubstrate of PKR. There is a loss-of-function mutation within K3L. By either truncating or by placing point mutations within the C-terminal portion of K3L protein, homologous to residues 79 to 83 in eIF-2a abolish PKR inhibitory activity.[31]

The term "attenuated vaccinia virus" or "modified vaccinia virus" means that the gene product or products which prevent the activation of PKR are lacking, inhibited or mutated such that PKR activation is not blocked. Preferably, the E3L gene and/or the K3L gene is not transcribed. Such attenuated or modified vaccinia virus would not be able to replicate in normal cells that do not have an activated Ras-pathway, however, it would be able to infect and replicate in cells having an activated Ras-pathway.

A "proliferative disorder" is any cellular disorder in which the cells proliferate more rapidly than normal tissue growth. Thus a "proliferating cell" is a cell that is proliferating more rapidly than normal cells. The proliferative disorder, includes but is not limited to neoplasms. A "neoplasm" is an abnormal tissue growth, generally forming a distinct mass, that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a neoplasm, also referred to as a "tumor", is intended to encompass hematopoietic neoplasms as well as solid neoplasms. Other proliferative disorders include, but are not limited to neurofibromatosis.

"Administration to a proliferating cell or neoplasm" indicates that the virus is administered in a manner so that it contacts the proliferating cells or cells of the neoplasm (also referred to herein as "neoplastic cells").

A "mammal suspected of having a proliferative disorder" means that the mammal may have a proliferative disorder or tumor or has been diagnosed with a proliferative disorder or tumor or has been previously diagnosed with a proliferative disorder or tumor, the tumor or substantially all of the tumor has been surgically removed and the mammal is suspected of harboring some residual tumor cells.

"Viral infection" or "virus infection" as used herein refers to infection by one or more of adenovirus, HSV, parapoxvirus orf virus, or vaccinia virus.

"Resistance" of cells to viral infection indicates that infection of the cells with the virus does not result in significant viral production or yield. Without being limited to any theory, resistance to viral infection is believed to be found at the level of gene translation, rather than at early transcription. While viral transcripts are produced, viral proteins are not expressed. It is thought that viral gene transcription in resistant cells correlated with phosphorylation of an approximately 65 kDa cell protein, determined to be double-stranded RNA-activated protein kinase (PKR), that was not observed in transformed cells. Phosphorylation of PKR lead to inhibition of translation.

The term "substantial lysis" means at least 10% of the proliferating cells are lysed, more preferably of at least 50% and most preferably of at least 75% of the cells are lysed. The percentage of lysis can be determined for tumor cells by measuring the reduction in the size of the tumor in the mammal or the lysis of the tumor cells in vitro.

"Anti-virus antibody" refers to an antibody which binds to a particular virus. For example, an anti-virus antibody may be an anti-adenovirus antibody, an anti-HSV antibody, an anti-vaccinia virus antibody or an anti-parapoxvirus orf virus antibody. The particular anti-virus antibody selected for use in the methods of this invention will correspond to the virus which is administered to the patient. For example, an anti-HSV antibody would be used in the method where a modified HSV is administered.

"Anti-antivirus antibodies," are antibodies directed against anti-virus antibodies. Anti-antivirus antibodies used in this invention are selected from anti-antiadenovirus antibodies, anti-antiHSV antibodies, anti-antivaccinia virus antibodies and anti-antiparapoxvirus orf virus antibodies. Such antibodies can be made by methods known in the art. See for example "Antibodies: A laboratory manual" E. Harlow and D. Lane, Cold Spring Harbor Laboratory (1988).

"IgG antibodies" refers to immunoglobulin G antibodies. IgG, the most abundant type of antibody, carries the major burden of neutralizing bacterial toxins and binding to microorganisms to enhance their phagocytosis.

"Humanized antibodies" refers to antibody molecules in which the amino acid sequence in the non-antigen binding regions has been altered so that the antibody more closely resembles a human antibody, and still retains its original binding ability.

The terms "immunosuppressant" or "immune suppressive agent" include conventional immunosuppressants, immunoinhibitors, antibodies, and conditions such as radiation therapy or HIV infection which result in compromise of the immune system.

"B-cells" refers to B-lymphocytes. There are two major subpopulations of B lymphocytes, B-1 and B-2 cells. B-1 cells are self-renewing and frequently secrete high levels of antibody which bind to a range of antigens (polyspecificity) with a relatively low affinity. The majority of B cells, B-2 cells, are directly generated from precursors in the bone marrow and secrete highly specific antibody.

"T-cells" refers to T-lymphocytes. T-cells differentiate within the thymus gland and are specialized to operate against cells bearing intracellular organisms. T-cells only recognize antigen when it is on the surface of a body cell.

It is believed that the virus uses the host cell's Ras pathway machinery to downregulate PKR and thus reproduce. FIG. 1 depicts the usurpation of the host cell Ras signalling pathway by adenovirus. As shown in FIG. 1, in both untransformed and Ras-activated cells, wild-type adenovirus (denoted with +) and VAI defective adenovirus (open circle) are both able to bind, internalize and undergo early transcription in a normal fashion.

During transcription, wild-type adenovirus (panel #1) is able to transcribe VAI RNAs that can bind to PKR without activating it. Because PKR is unable to displace these short, double stranded RNAs (dsRNAs), PKR is unable to interact with subsequent longer transcripts and autophosphorylate. Thus, the virus is able to replicate and produce progeny virus.

When attempting to replicate in untransformed cells (panel #2), modified adenovirus is unable to produce the VAI RNAs which bind to PKR. Thus, PKR can interact with longer viral transcripts that are capable of causing autophosphorylation and activate PKR. The activated PKR is then able to phosphorylate the translation initiation factor eIF-2α and block translation of viral genes that lead to abortive viral replication.

Panel #3 shows the modified adenovirus infecting a Ras-activated cancer cell where the outcome is different from the outcome described in panels #1 and #2. In the Ras-transformed cells, it has been observed that PKR is unable to undergo phosphorylation or that phosphorylation is rapidly reversed by an element of the activated Ras pathway. The result in the Ras-activated cells is that the modified form of the adenovirus is able to translate its viral genes and complete replication without the transcription of the VAI RNAs. The surprising result in these cells is oncolysis.

As is known in the art, the implantation of human tumor cells into SCID mice is recognized as a well known model system for testing the effectiveness of various anti-tumor agents in humans. It has previously been shown that pharmaceuticals effective against human tumors implanted into SCID mice can be predictive of their effectiveness against the same tumors in humans.

Based upon these discoveries, Applicants have developed methods for treating cell proliferative disorders in mammals wherein the cells have an activated Ras-pathway. Representative mammals include dogs, cats, sheep, goats, cattle, horses, pigs, non-human primates, and humans. In a preferred embodiment, the mammal is a human.

METHODS OF THE INVENTION

In the methods of the invention, modified virus is administered to proliferating cells having an activated Ras-pathway in the individual mammal. Representative types of modified virus include adenovirus, HSV, parapoxvirus orf virus, or vaccinia virus which infect humans. In a preferred embodiment, modified adenovirus is used.

The virus may be a recombinant virus from two or more types of viruses with differing pathogenic phenotypes such that it contains different antigenic determinants thereby reducing or preventing an immune response by a mammal previously exposed to a virus subtype. Such recombinant virions can be generated by co-infection of mammalian cells with different subtypes of virus with the resulting resorting and incorporation of different subtype coat proteins into the resulting virion capsids.

The virus may be modified by incorporation of mutated coat proteins into the virion outer capsid. The proteins may be mutated by replacement, insertion or deletion. "Replacement" includes the insertion of different amino acids in place of the native amino acids. "Insertions" include the insertion of additional amino acid residues into the protein at one or more locations. "Deletions" include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in virus infected mammalian cells in vitro such as COS1 cells will result in the incorporation of the mutated protein into the virus virion particle The virus is preferably a virus modified to reduce or eliminate an immune reaction to the virus. Such modified virus are termed "immunoprotected virus". Such modifications could include packaging of the virus in a liposome, a micelle or other vehicle to mask the virus from the mammals immune system.

At least some of the cells of the proliferative disorder have a mutation in which the Ras gene (or an element of the Ras signaling pathway) is activated, either directly (e.g., by an activating mutation in Ras) or indirectly (e.g., by activation of an upstream element in the Ras pathway). Activation of an upstream element in the Ras pathway includes, for example, transformation with epidermal growth factor receptor (EGFR) or Sos. A proliferative disorder that results, at least in part, by the activation of Ras, an upstream element of Ras, or an element in the Ras signalling pathway is referred to herein as a "Ras-mediated proliferative disorder".

One neoplasm that is particularly susceptible to treatment by the methods of the invention is pancreatic cancer, because of the prevalence of Ras-mediated neoplasms associated with pancreatic cancer. Other neoplasms that are particularly susceptible to treatment by the methods of the invention include breast cancer, central nervous system cancer (e.g., neuroblastoma and glioblastoma), peripheral nervous system cancer, lung cancer, prostate cancer, colorectal cancer, thyroid cancer, renal cancer, adrenal cancer, liver cancer, lymphoma and leukemia. One proliferative disorder that is particularly susceptible to treatment by the methods of this invention include neurofibromatosis 1 because of the activation of the Ras pathway.

The virus is administered to a proliferating cell or neoplasm in a manner so that it contacts the proliferating cells or cells of the neoplasm or neoplastic cells. The route by which the virus is administered, as well as the formulation, carrier or vehicle, will depend on the location as well as the type of the neoplasm. A wide variety of administration routes can be employed. For example, for a solid neoplasm that is accessible, the virus can be administered by injection directly to the neoplasm. For a hematopoietic neoplasm, for example, the virus can be administered intravenously or intravascularly. For neoplasms that are not easily accessible within the body, such as metastases or brain tumors, the virus is administered in a manner such that it can be transported systemically through the body of the mammal and thereby reach the neoplasm (e.g., intrathecally, intravenously or intramuscularly).

Alternatively, the virus can be administered directly to a single solid neoplasm, where it then is carried systemically through the body to metastases. The virus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

Virus can be administered systemically to mammals which are immune compromised or which have not developed immunity to the virus epitopes. In such cases, virus administered systemically, i.e. by intravenous injection, will contact the proliferating cells resulting in lysis of the cells.

Immunocompetent mammals previously exposed to a particular virus, such as modified adenovirus, modified HSV, modified vaccinia virus and modified parapoxvirus orf virus, may have developed humoral and/or cellular immunity to that virus. Nevertheless, it is contemplated that direct injection of the virus into a solid tumor in immunocompetent mammals will result in the lysis of the neoplastic cells.

When the virus is administered systemically to immunocompetent mammals, the mammals may produce an immune response to the virus. Such an immune response may be avoided if the virus is of a subtype to which the mammal has not developed immunity, or the virus has been modified as previously described herein such that it is immunoprotected, for example, by protease digestion of the outer capsid or packaging in a micelle.

It is contemplated that the virus may be administered to immunocompetent mammals immunized against the virus in conjunction with the administration of anti-antivirus antibodies. Such anti-antivirus antibodies may be administered prior to, at the same time or shortly after the administration of the virus. Preferably an effective amount of the anti-antivirus antibodies are administered in sufficient time to reduce or eliminate an immune response by the mammal to the administered virus.

Alternatively, it is contemplated that the immunocompetency of the mammal against the virus may be suppressed either by the prior or co-administration of pharmaceuticals known in the art to suppress the immune system in general (Cuff et al., "Enteric reovirus infection as a probe to study immunotoxicity of the gastrointestinal tract" Toxicological Sciences 42(2):99-108 (1998)) or alternatively the administration of such immunoinhibitors as anti-antivirus antibodies.

The humoral immunity of the mammal against the virus may also be temporarily reduced or suppressed by plasmaphoresis of the mammals blood to remove the anti-virus antibodies. The anti-virus antibodies removed by this process correspond to the virus selected for administration to the patient. For example, if a modified parapox orf virus is selected for administration, then the anti-parapox orf virus antibodies will be removed. The humoral immunity of the mammal against the virus may additionally be temporarily reduced or suppressed by the intravenous administration of non-specific immunoglobulin to the mammal.

Other agents are known to have immunosuppressant properties as well (see, e.g., Goodman and Gilman, 7" Edition, page 1242, the disclosure of which is incorporated herein by reference). Such immunoinhibitors also include anti-antivirus antibodies, which are antibodies directed against anti-virus antibodies. Anti-antivirus antibodies used in this invention are selected from anti-antiadenovirus antibodies, anti-antiHSV antibodies, anti-antivaccinia virus antibodies and anti-antiparapoxvirus orf virus antibodies. Such antibodies can be made by methods known in the art. See for example "Antibodies: A laboratory manual" E. Harlow and D. Lane; Cold Spring Harbor Laboratory (1988).

Such anti-antivirus antibodies may be administered prior to, at the same time or shortly after the administration of the virus. Preferably an effective amount of the anti-antivirus antibodies are administered in sufficient time to reduce or eliminate an immune response by the mammal to the administered virus.

In yet other methods of the invention, a virus selected from the group consisting of modified adenovirus, modified HSV, modified vaccinia virus and modified parapoxvirus orf virus is administered to Ras-mediated proliferating cells in the individual mammal. In one embodiment of this invention a course of this therapy is administered one or more times. Following the first administration of virus therapy particular immune constituents that may interfere with subsequent administrations of virus are removed from the patient. These immune constituents include B cells, T cells, antibodies, and the like.

Removal of either the B cell or T cell population can be accomplished by several methods. In one method, the blood may be filtered and heme-dialysis may be performed. Another method is the filtration of the blood coupled with extra corporeal compounds that can remove the cell populations, for example, with immobilized antibodies that recognize specific receptors on the cell population which is to be remove. Yet another method for removal of a cell population is by immune suppression. This can be done by first line radiation therapy or by cyclic steroids such as cyclosporin.

Selective removal of anti-virus antibodies can also prevent the patient's immune system from removing therapeutically administered virus. Preventing antibody interaction with the administered virus may also assist systemic treatment strategies. Antibodies can be removed by several methods, including heme-dialysis and passing the blood over immobilized virus (selective antibody removal); by removal of all IgG antibodies by heme-dialysis and passing the blood over immobilized protein A (commercially available as PROSORBA, Cypress Bioscience, San Diego, Calif.); or by administration of humanized anti-idiotypic antibodies, where the idiotype is against the virus to be administered (e.g., a virus selected from the group consisting of modified adenovirus, modified HSV, modified vaccinia virus and modified parapoxvirus orf virus).

Another method of this invention is to allow virus to act systemically without impairing normal immune function by masking or impairing immune recognition of virus. To prevent the patient's immune system from recognizing the administered virus, the virus may be coated with non-virotoxic humanized antibodies, such as coating with the $F_{ab}$ portion of the antibody, or coated in a micelle.

Additionally, the virus may be treated with chymotrypsin to yield an infectious subviral particle (ISVP). An ISVP may be used either alone or in combination with whole virus to provide an agent that is either poorly recognized has not been previously prevented by the patient's immune system.

Another embodiment of this invention includes the removal of virus from the patient following administration. Since this method may be used on patients that are either immune suppressed or immune incompetent, it may be of importance to remove virus from the blood stream following the course of treatment. Virus may be removed by affinity chromatography using extra corporeal anti-virus antibodies associated with heme dialysis, B-cell proliferative agents, or adjuvants to stimulate immune response against the virus such as UV inactivated virus or Freund's adjuvant.

Pharmaceutical Compositions

This invention also includes pharmaceutical compositions which contain, as the active ingredient, one or more of the viruses associated with "pharmaceutically acceptable carriers or excipients." This invention also includes pharmaceutical compositions which contain, as the active ingredient, one or more immunosuppressants or immunoinhibitors and one or more of the viruses associated with "pharmaceutically acceptable carriers or excipients."

In making the compositions of this invention, the active ingredient(s), e.g., the virus and/or immunosuppressant or immunoinhibitor, are usually mixed with an excipient, diluted by an excipient or enclosed within such a carrier which can be in the form of a capsule, sachet, paper or other container.

When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/virus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the virus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

Kits of Parts

The virus or the pharmaceutical composition comprising the virus may be packaged into convenient kits providing the necessary materials packaged into suitable containers. It is contemplated the kits may also include chemotherapeutic agents and/or anti-antivirus antibody.

The immunosuppressant or immunoinhibitor and virus or the pharmaceutical composition comprising the immunosuppressant or immunoinhibitor and virus may be packaged into convenient kits providing the necessary materials packaged into suitable containers. It is contemplated the kits may also include chemotherapeutic agent.

Administration of Virus

The virus is administered in an amount that is sufficient to treat the proliferative disorder (e.g., an "effective amount"). A proliferative disorder is "treated" when administration of virus to the proliferating cells effects lysis of the proliferating cells. This may result in a reduction in size of the neoplasm, or in a complete elimination of the neoplasm. The reduction in size of the neoplasm, or elimination of the neoplasm, is generally caused by lysis of neoplastic cells ("oncolysis") by the virus.

Preferably, the effective amount is that amount able to inhibit tumor cell growth. Preferably the effective amount is from about 1.0 pfu/kg body weight to about $10^{15}$ pfu/kg body weight, more preferably from about $10^2$ pfu/kg body weight to about $10^{13}$ pfu/kg body weight. For example, for treatment of a human, approximately $10^2$ to $10^{17}$ plaque forming units (PFU) of virus can be used, depending on the type, size and number of tumors present. The effective amount will be determined on an individual basis and may be based, at least in part, on consideration of the type of virus; the chosen route of administration; the individual's size, age, gender; the severity of the patient's symptoms; the size and other characteristics of the neoplasm; and the like. The course of therapy may last from several days to several months or until diminution of the disease is achieved.

The virus can be administered in a single dose, or multiple doses (i.e., more than one dose). The multiple doses can be administered concurrently, or consecutively (e.g., over a period of days or weeks). The virus can also be administered to more than one neoplasm in the same individual.

The compositions are preferably formulated in a unit dosage form, each dosage containing from about $10^2$ pfus to about $10^{13}$ pfus of the virus. The term "unit dosage forms" refers to physically discrete units suitable as unitary dosages for human subjects and other mammals, each unit containing a predetermined quantity of virus calculated to produce the desired therapeutic effect, in association with a suitable pharmaceutical excipient.

It has been found that the virus is effective for the treatment of solid neoplasms in immunocompetent mammals. Administration of unmodified virus directly to the neoplasm results in oncolysis of the neoplastic cells and reduction in the size of the tumor.

It is contemplated that the virus may be administered in conjunction with surgery or removal of the neoplasm. Therefore, provided herewith are methods for the treatment of a solid neoplasm comprising surgical removal of the neoplasm and administration of a virus at or near to the site of the neoplasm.

It is contemplated that the virus may be administered in conjunction with or in addition to radiation therapy.

It is further contemplated that the virus of the present invention may be administered in conjunction with or in addition to known anti-cancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs. In one embodiment of the invention, a method is provided for reducing the growth of metastastic tumors in a mammal comprising administering an effective amount of a virus to the mammal.

Administration of Virus with Immunosuppressant or Immunoinhibitor

The immunosuppressant or immunoinhibitor is administered in an appropriate amount and using an appropriate schedule of administration sufficient to result in immunosuppression or immunoinhibition of the mammal's immune system. Such amounts and schedules are well known to those of skill in the art.

The immunosuppressant or immunoinhibitor and virus can be administered in a single dose, or multiple doses (i.e., more than one dose). The multiple doses can be administered concurrently, or consecutively (e.g., over a period of days or weeks). The virus can also be administered to more than one neoplasm in the same individual.

The compositions are preferably formulated in a unit dosage form, each dosage containing an appropriate amount of immunosuppressant or immunoinhibitor and from about $10^2$ pfus to about $10^{13}$ pfus of the virus. The term "unit dosage forms" refers to physically discrete units suitable as unitary dosages for human subjects and other mammals, each unit containing a predetermined quantity of virus calculated to produce the desired therapeutic effect, in association with a suitable pharmaceutical excipient.

As mentioned above, it has been found that the virus is effective for the treatment of solid neoplasms in immunocompetent mammals. Administration of unmodified virus directly to the neoplasm results in oncolysis of the neoplastic cells and reduction in the size of the tumor in immunocompetent animals. When animals are rendered immunosuppressed or immunodeficient in some way, systemic administration of virus will be more effective in producing oncolysis.

It is contemplated that the virus may be administered in conjunction with or in addition to radiation therapy which renders the mammal immunosuppressed. It is further contemplated that the virus and immunosuppressant or immunoinhibitor may be administered in conjunction with or in addition to known anti-cancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs.

The virus and immunosuppressants of the present invention are contemplated to reduce the growth of tumors that are metastatic. In an embodiment of the invention, a method is provided for reducing the growth of metastatic tumors in a mammal comprising administering an effective amount of a virus to the immunosuppressed mammal.

It is contemplated that the selected virus may be administered to immunocompetent mammals immunized against the selected virus in conjunction with the administration of immunosuppressants and/or immunoinhibitors. For example, if a modified vaccinia virus is selected then the immunocompetent mammal is immunized against vaccinia virus. Such immunosuppressants and immunoinhibitors are known to those of skill in the art and include such agents as cyclosporin, rapamycin, tacrolimus, mycophenolic acid, azathioprine and their analogs, and the like.

Utility

The viruses of the present invention may be used for a variety of purposes. They may be used in methods for treating Ras-mediated proliferative disorders in a mammal. The virus may be used to reduce or eliminate neoplasms. They may be used in methods for treating metastases. They may be used in conjunction with known treatments for cancer including surgery, chemotherapy and radiation.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

μM=micromolar
mM=millimolar
M=molar
ml=milliliter
μl=microliter
mg=milligram
μg=microgram
DNA=deoxyribonucleic acid
RNA=ribonucleic acid
PAGE=polyacrylamide gel electrophoresis
rpm=revolutions per minute
FBS=fetal bovine serum
DTT=dithiothrietol
SDS=sodium dodecyl sulfate
PBS=phosphate buffered saline
DMEM=Dulbecco's modified Eagle's medium
α-MEM=α-modified Eagle's medium
β-ME=β-mercaptoethanol
MOI=multiplicity of infection
PFU=plaque forming units MAPK=MAP kinase
phosph-MAPK=phosphorylated-MAP kinase
HRP=horseradish-peroxidase
PKR=double-stranded RNA activated protein kinase
RT-PCR=reverse transcriptase-polymerase chain reaction
GAPDH=glyceraldehyde-3-phosphate dehydrogenase
EGFR=epidermal growth factor receptors
MEK kinase=mitogen-activated extracellular signal-regulated kinase
DMSO=dimethylsulfoxide
SCID=severe combined immunodeficiency General Methods Cells and Virus 293 cells (human embryonic kidney (HEK) cells (available from ATCC)) are grown as monolayers in Dulbecco's modified Eagle's medium (DMEM, GIBCO Laboratories) supplemented with 10% newborn calf serum (NC) and as suspension cultures in minimal essential medium (SMEM, GIBCO Laboratories) supplemented with 5% NCS.

VAI mutant adenovirus are propagated in suspension cultures of 293 cells maintained in the same medium. Plaque assays are performed on HeLa and 293 monolayers in DMEME containing 0.7% agarose, 2% NCS, 2 mM L-glutamine, MEM nonessential acids (GIBCO Laboratories), and 25 mM $MgCl_2$.

Example 1

In Vivo Oncolytic Capability of Adenovirus Against Human Breast Cancer-Derived Cell Lines In vivo studies are carried out using human breast carcinoma cells in a SCID mouse model. Female SCID mice are injected with $1 \times 10^6$ human breast carcinoma MDA-MB468 cells in two subcutaneous sites, overlying both hind flanks. Palpable tumors are evident approximately two to four weeks post injection. Undiluted adenovirus is injected into the right side tumor mass in a volume of 20 μl at a concentration of $1.0 \times 10^7$ PFU/ml.

Example 2

Susceptibility of Additional Human Tumors to Adenovirus Oncolysis

Cells and Virus

All cell lines are grown in Dulbecco's modified Eagle's medium (DMEM) containing 10% fetal bovine serum (FBS). The adenovirus used in these studies is propagated in suspension cultures of L cells and purified as described above.

Cytopathic Effects of Adenovirus on Cells

Confluent monolayers of cells are infected with adenovirus at a multiplicity of infection (MOI) of approximately 40 plaque forming units (PFU) per cell.

Pictures are taken at 36 hour postinfection for both adenovirus-infected and mock infected cells.

Immunofluorescent Analysis of Adenovirus Infection

For the immunofluorescent studies the cells are grown on coverslips, and infected with adenovirus at a multiplicity of infection (MOI) of ~10 PFU/cell or mock-infected as described above. At various times postinfection, cells are fixed in an ethanol/acetic acid (20/1) mixture for 5 minutes, then rehydrated by subsequential washes in 75%, 50% and 25% ethanol, followed by 4 washes with phosphate-buffered saline (PBS). The fixed and rehydrated cells are then exposed to the primary antibody (rabbit polyclonal anti-adenovirus serum diluted 1/100 in PBS) for 2 hr at room temperature. Following 3 washes with PBS, the cells are exposed to the secondary antibody [goat anti-rabbit IgG (whole molecule) fluorescein isothiocyanate (FITC) conjugate diluted 1/100 in PBS containing 10% goat serum and 0.005% Evan's Blue counterstain] for 1 hour at room temperature. Finally, the fixed and treated cells are washed 3 more times with PBS, followed by 1 wash with double-distilled water, dried and mounted on slides in 90% glycerol containing 0.1% phenylenediamine, and viewed with a Zeiss Axiophot microscope mounted with a Carl Zeiss camera (magnification for all pictures was 200×).

Infection of Cells and Quantitation of Virus

Confluent monolayers of cells grown in 24-well plates are infected with adenovirus at an estimated multiplicity of 10 PFU/cell. After 1 hour incubation at 37° C., the monolayers are washed with warm DMEM-10% FBS, and then incubated in the same medium. At various times postinfection, a mixture of NP-40 and sodium deoxycholate is added directly to the medium on the infected monolayers to final concentrations of 1% and 0.5%, respectively. The lysates are then harvested and virus yields are determined by plaque titration on L-929 cells.

Radiolabelling of Adenovirus-Infected Cells and Preparation of Lysates

Confluent monolayers of cells are infected with adenovirus (MOI ~10 PFU/cell). At various times postinfection, the media is replaced with methionine-free DMEM containing 10% dialyzed PBS and 0.1 mCi/ml [$^{35}$S]methionine. After further incubation for 1 hour at 37° C., the cells are washed in phosphate-buffered saline (PBS) and lysed in the same buffer containing 1% Triton X-100, 0.5% sodium deoxycholate and 1 mM EDTA. The nuclei are then removed by low speed centrifugation and the supernatants stored at 70° C. until use.

Immunoprecipitation and SDS-PAGE Analysis

Standard immunoprecipitation of [$^{35}$S]-labelled adenovirus-infected cell lysates with anti-adenovirus serum is done. Immunoprecipitates are analyzed by discontinuous SDS-PAGE according to the protocol of Laemmli (Laemmli, U. K., (1970) *Nature*, 227:680-685).

Breast Cancer

The c-erbB-2/neu gene encodes a transmembrane protein with extensive homology to the EGFR that is overexpressed in 20-30% of patients with breast cancer (Yu, D. et al. (1996) *Oncogene* 13:1359). Ras activation, either through point mutations or through augmented signaling cascade elements upstream of Ras (including the c-erbB-2/neu homologue EGFR) ultimately creates a hospitable environment for virus replication, an array of cell lines derived from human breast cancers are assayed for adenovirus susceptibility. The cell lines included MDA-MD-435SD (ATCC deposit HTB-129), MCF-7 (ATCC deposit HTB-22), T-27-D (ATCC deposit HTB-133), BT-20 (ATCC deposit HTB-19), HBL-100 (ATCC deposit HTB-124), MDA-MB-468 (ATCC deposit HTB-132), and SKBR-3 (ATCC deposit HTB-30).

Based upon induction of cytopathic effects and viral protein synthesis as measured by radioactive metabolic labeling and immunofluorescence as described above, sensitivity to infection may be determined.

Brain Glioblastoma

Human brain glioblastoma cell lines A-172, U-118, U-178, U-563, U-251, U-87 and U-373 (these cells are a generous gift from Dr. Wee Yong, University of Calgary) are tested to determine the susceptibility to adenovirus infection.

To assess the sensitivity of these cells to adenovirus, cells are grown to 80% confluency and are then challenged with adenovirus at a multiplicity of infection (MOI) of 10. Within a period of 48 hours, widespread cytopathic effects will be seen. To demonstrate further that the lysis of these cells is due to replication of adenovirus, the cells are then pulse-labeled with [$^{35}$S]methionine for three hour periods at various times post-infection and proteins are analyzed by sodium dodecyl sulfate-polyacrylamide gel electrophoresis (SDS-PAGE) as described above.

U-87 cells are also introduced as human tumor xenografts into the hind flank of 10 SCID mice. U-87 cells are grown in Dulbecco's modified Eagle's medium containing 10% fetal bovine serum, as described above. Cells are harvested, washed, and resuspended in sterile PBS; $2.0 \times 10^6$ cells in 100 µl, and are injected subcutaneously at a site overlying the hind flank in five- to eight-week old male SCID mice (Charles River, Canada). Tumor growth is measured twice weekly for a period of four weeks.

To determine if there is viral spread beyond the tumor mass, immunofluorescent microscopy using antibodies directed against total adenovirus proteins is conducted, as described above, on paraffin sections of the tumor and adjoining tissue.

Since most tumors are highly vascularized, it is likely that some virus may enter the blood stream following the lysis of the infected tumor cells. To determine if there is systemic spread of the virus, blood is harvested from the treated and control animals, serially diluted for subsequent plaque titration, and the concentration of infectious virus in the blood is determined.

The high degree of tumor specificity of the virus, combined with systemic spread, suggest that adenovirus can replicate in glioblastoma tumors remote from the initially infected tumor. SCID mice are implanted bilaterally with U-87 human tumor xenografts on sites overlying each hind flank of the animals. These tumors are allowed to grow until they measure $0.5 \times 0.5$ cm. The left-side tumors are then injected with a single dose ($1 \times 10^7$ pfu) of adenovirus in treated animals (n=5); control animals (n=7) are mock-treated with UV-inactivated virus. Tumors are again measured twice weekly for a period of four weeks.

Pancreatic Carcinoma

Cell lines derived from pancreatic cancer are investigated for their susceptibility to adenovirus infection, using processes described above. The cell lines included Capan-1 (ATCC deposit HTB-79), BxPC3 (ATCC deposit CRL 1687), MIAPACA-2 (ATCC deposit CRL-1420), PANC-1 (ATCC deposit CRL-1469), AsPC-1 (ATCC deposit CRL-1682) and Hs766T (ATCC deposit HTB-134).

The assays described above may be modified by one skilled in the art to test the susceptibility of cells to other types of virus, such as HSV, vaccinia virus and parapoxvirus orf virus.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A kit comprising a modified adenovirus in a pharmaceutically acceptable excipient, an anti-anti-adenovirus antibody, and a chemotherapeutic agent, wherein the gene product or products that prevent activation of PKR are lacking, inhibited or mutated in the modified adenovirus such that PKR activation is not blocked.

2. The kit of claim 1, wherein the modified adenovirus comprises a mutation in or lacks the VAI RNA gene.

3. A kit comprising a modified adenovirus in a pharmaceutically acceptable excipient and an anti-anti-adenovirus antibody, wherein the gene product or products that prevent activation of PKR are lacking, inhibited or mutated in the modified adenovirus such that PKR activation is not blocked.

4. A composition comprising a modified adenovirus in a pharmaceutically acceptable excipient, an anti-anti-adenovirus antibody and a chemotherapeutic agent, wherein the gene product or products that prevent activation of PKR are lacking, inhibited or mutated in the modified adenovirus such that PKR activation is not blocked.

5. The composition of claim 4, wherein the modified adenovirus comprises a mutation in or lacks the VAI RNA gene.

6. The composition of claim 4, wherein the modified adenovirus is immunoprotected.

7. A composition comprising a modified adenovirus in a pharmaceutically acceptable excipient and an anti-anti-adenovirus antibody, wherein the gene product or products that prevent activation of PKR are lacking, inhibited or mutated in the modified adenovirus such that PKR activation is not blocked.

8. The composition of claim 7, wherein the modified adenovirus comprises a mutation in or lacks the VAI RNA gene.

9. The composition of claim 7, wherein the modified adenovirus is immunoprotected.

* * * * *